US006973163B2

(12) United States Patent
Arakawa

(10) Patent No.: US 6,973,163 B2
(45) Date of Patent: Dec. 6, 2005

(54) RADIOGRAPHY SYSTEM AND MACHINE READABLE MEDIUM STORING PROGRAM

(75) Inventor: Satoshi Arakawa, Kanagawa (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 74 days.

(21) Appl. No.: 10/800,772

(22) Filed: Mar. 16, 2004

(65) Prior Publication Data

US 2004/0184581 A1     Sep. 23, 2004

(30) Foreign Application Priority Data

Mar. 19, 2003  (JP) ............................. 2003-076470

(51) Int. Cl.[7] ............................................. G01N 23/04
(52) U.S. Cl. ...................................... 378/63; 378/98.5
(58) Field of Search ................................. 376/63, 98.5

(56) References Cited

U.S. PATENT DOCUMENTS 4,246,607 A * 1/1981 Vijverberg ................. 378/98.5
6,504,897 B1 * 1/2003 Yonekawa ................... 378/63

FOREIGN PATENT DOCUMENTS

JP          55-012429 A    1/1980

OTHER PUBLICATIONS

M.J. Yaffe, J.A. Rowlands, "X-ray detectors for digital radiography", Phys. Med. Biol. 42, 1-39, 1997, UK.

* cited by examiner

Primary Examiner—Craig E. Church
Assistant Examiner—Jurie Yun
(74) Attorney, Agent, or Firm—Sughrue Mion, PLLC

(57) ABSTRACT

A radiography system and the machine readable medium storing program for accurately determining the type of the object taken by the radiography. The radiography system includes: a radiographic image receiving section for receiving the radiographic image of the object using the radiation; an optical image receiving section for detecting light from the object, and for receiving the optical image of the object; an object type determination section for determining an object type of the radiographic image received by the radiographic image receiving section based on the optical image received by the optical image receiving section; and an image storage section storing thereon the radiographic image received by the radiographic image receiving section in association with the object type determined by the object type determination section, and for storing the radiographic image and the object type, being associated with each other.

10 Claims, 5 Drawing Sheets

FIG. 5

| ID NO. STORAGE REGION 500 | IMAGING AREA STORAGE REGION 501 | IMAGING DIRECTION STORAGE REGION 502 | RADIOGRAPHIC IMAGE DATA STORAGE REGION 503 | INCIDENTAL INFORMATION STORAGE REGION 504 |
|---|---|---|---|---|
| 001 | CHEST | PA | RADIOGRAPHIC_IMAGE_001.JPG | LUDWIG BEETHOVEN |
| 002 | LEFT HAND | PA | RADIOGRAPHIC_IMAGE_002.JPG | WOLFGANG MOZART |
| ... | ... | ... | ... | ... |

134

RADIOGRAPHY SYSTEM AND MACHINE READABLE MEDIUM STORING PROGRAM

This patent application claims priority from a Japanese patent application No. 2003-076470 filed on Mar. 19, 2003, the contents of which are incorporated herein by reference.

BACKGROUND OF THE INVENTION

1. Field of the Invention

The present invention relates to a radiography system and a machine readable medium storing program. More particularly, the present invention relates to a radiography system and a machine readable medium storing program for determining type of an object examined by the radiography.

2. Description of the Related Art

Radiographic image such as X-ray image is widely used for diagnosis. Conventionally, the radiographic image is obtained by exposing a phosphor to radiation transmitted through the object, exposing a silver halide film to a visible light emitted from the phosphor, and developing the film like a conventional photographic film.

Recently, a method of detecting an image using a photostimulable phosphor has been developed, which does not require a silver halide film (cf. Japanese Patent Application Publication (Laid-Open) No. 55-012429). By this method, after exposing the photostimulable phosphor to the radiation transmitted through the object, radiation energy, which will be freed as light, is emitted by exciting the photostimulable phosphor by light energy or heat energy. Then, the light is converted into electric signal by photoelectric conversion, and the image signal is obtained. Moreover, the method of detecting the radiographic image using many semiconductor elements is also developed (cf. M. J. Yaffe, J. A. Rowlands, "X-ray detectors for digital radiography", Phys. Med. Biol. 42, 1–39, 1997).

As for the radiographic image taken by the above-described methods, there are some cases that it is difficult to determine from the radiographic image whether the image is taken from back of the patient or from front of the patient, which part of the patient is taken, etc. Therefore, in the conventional radiography system, when a doctor takes the radiographic image of an object, the information about the image, such as the direction from which the image of the patient's body was taken (to be referred to as "imaging direction" hereinafter), or the area of the patient's body that was taken (to be referred to as "imaging area" hereinafter), has to be recorded manually with the radiographic image to make the diagnosis with the image easier.

However, according to the conventional method, if a doctor or a radiological technician mistakenly records the imaging direction and the imaging area with the radiographic image, there are no means for correcting the mistake. Consequently, the radiographic image, of which the imaging direction or the imaging area is mistakenly recorded, may be used for the diagnosis.

SUMMARY OF THE INVENTION

Therefore, it is an object of the present invention to provide a radiography system and a machine readable medium storing program which can solve the foregoing problems. The above and other objects can be achieved described in the independent claim. The dependent claims define further advantageous and exemplary combinations of the present invention.

According to a first aspect of the present invention, there is provided a radiography system for acquiring a radiographic image of an object using radiation. The radiography system includes: a radiographic image receiving section for receiving the radiographic image of the object using the radiation; an optical image receiving section for detecting light from the object, and for receiving the optical image of the object; an object type determination section for determining an object type (imaging direction and imaging area) of the radiographic image received by the radiographic image receiving section based on the optical image received by the optical image receiving section; and an image storage section storing thereon the radiographic image received by the radiographic image receiving section in association with the object type determined by the object type determination section, and for storing the radiographic image and the object type, being associated with each other.

The object type determination section may determine a direction from which the radiographic image of the object, which is received by the radiographic image receiving section, is taken based on the optical image received by the optical image receiving section, and the image storage section may store the radiographic image received by the radiographic image receiving section in association with the imaging direction determined by the object type determination section. For example, the imaging direction is AP, PA, lateral, oblique, etc.

The object type determination section may determine an area of the object on the radiographic image received by the radiographic image receiving section based on the optical image received by the optical image receiving section, and the image storage section may store the radiographic image received by the radiographic image receiving section in association with the imaging area determined by the object type determination section. For example, the imaging area is head, chest, right leg, left leg, etc.

The radiography system may further include a template image storage section storing thereon a plurality of template images, each of which is associated with the object type, and the object type determination section may determine the object type by comparing the optical image received by the optical image receiving section with each of the plurality of template images stored on the template image storage section.

An area of the optical image received by the optical image receiving section may surround an area of the radiographic image to be received by the radiographic image receiving section. The optical image receiving section may receive the optical image including an image of the object and an image of an area surrounding the object. Alternatively, an area of the optical image received by the optical image receiving section may be substantially the same as an area of the radiographic image to be received by the radiographic image receiving section. For example, the optical image is an image taken by a visible-light camera or an infrared camera, and it may irradiate visible light or infrared radiation to the object if required. Since the infrared radiation is not visible, the irradiation of the infrared radiation does not hinder a radiographer from checking an exposure indication light.

The radiography system may further include a dosage adjustment section for adjusting dose of the radiation irradiating to the object in accordance with the object type determined by the object type determination section, and the radiographic image receiving section may receive the radiographic image of the object after the dosage adjustment section adjusts the dose of the radiation.

According to a second aspect of the present invention, there is provided a machine readable medium storing thereon a program for causing a radiography system to acquire a radiographic image of an object using radiation. The program includes modules configured to execute steps of: receiving the radiographic image of the object using the radiation; receiving the optical image of the object by detecting light emitted from the object; determining an object type of the radiographic image received in the radiographic image receiving step based on the optical image received by in the optical image receiving step; associating the radiographic image received in the radiographic image receiving step with the object type determined in the object type determination section; and storing the radiographic image and the object type, being associated with each other in the associating step.

The machine readable medium may further include a module configured to execute a step of adjusting dose of the radiation irradiating to the object in accordance with the object type determined in the object type determination step, and the radiographic image receiving step may be conducted after the dosage adjustment step.

The summary of the invention does not necessarily describe all necessary features of the present invention. The present invention may also be a sub-combination of the features described above.

BRIEF DESCRIPTION OF THE DRAWINGS

FIG. 5 is a table showing data structure of data stored on an image storage section.

DETAILED DESCRIPTION OF THE INVENTION

The invention will now be described based on the preferred embodiments, which do not intend to limit the scope of the present invention, but exemplify the invention. All of the features and the combinations thereof described in the embodiment are not necessarily essential to the invention.

Figure 1:
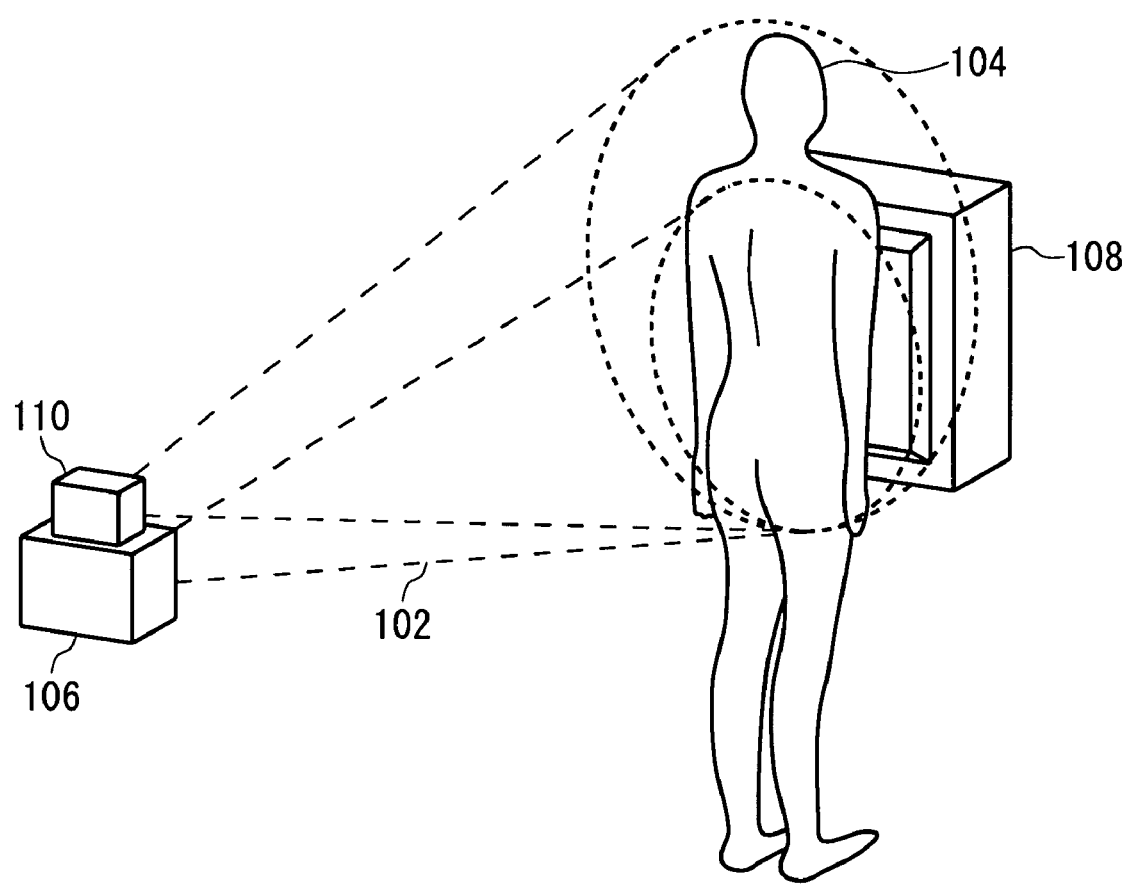
FIG. 1 is an external view exemplary showing a radiography system.

FIG. 1 is an external view exemplary showing a radiography system 100 according to an embodiment of the present invention. The radiography system 100 includes: a radiation source 106 for generating a radiation 102 and irradiating the radiation to an object 104; a radiographic image receiving section 108 for receiving a radiographic image of the object 104 using the radiation 102 irradiating from the radiation source 106; and an optical image receiving section 110 for detecting light from the object 104 and receiving the optical image of the object 104. For example, the radiographic image receiving section 108 is an imaging reader. Moreover, the radiation 102 is an X-ray, an alpha ray, a beta ray, a gamma ray, etc.

For example, the optical image receiving section 110 is a CCD camera for detecting visible light and receiving an image, or an infrared camera for detecting infrared radiation and receiving an image. Moreover, it is preferable that both the optical image receiving section 110 and the radiation source 106 are positioned at substantially the same position and face the object 104. In addition, although the radiography system 100 depicted in FIG. 1 includes one optical image receiving section 110, it may include a plurality of optical image receiving sections 110.

In the radiography system 100, the imaging direction and the imaging area of the radiographic image are detected based on the optical image received by the optical image receiving section 110. For example, it is detected whether the radiation 102 travels from front to back of a patient (AP) or from back to front of the patient (PA), whether the radiation 102 travels from dorsum to palm of a patient's hand (PA) or from palm to dorsum of the patient's hand (AP), or whether the object 104 is a right hand or a left hand. Then, the detected imaging direction and the imaging area are stored in association with the radiographic image received by the radiographic image receiving section 108 based on the optical image received by the optical image receiving section 110. Therefore, the imaging direction and the imaging area are recorded correctly, and appropriate diagnosis is provided to the patient.

Figure 2:
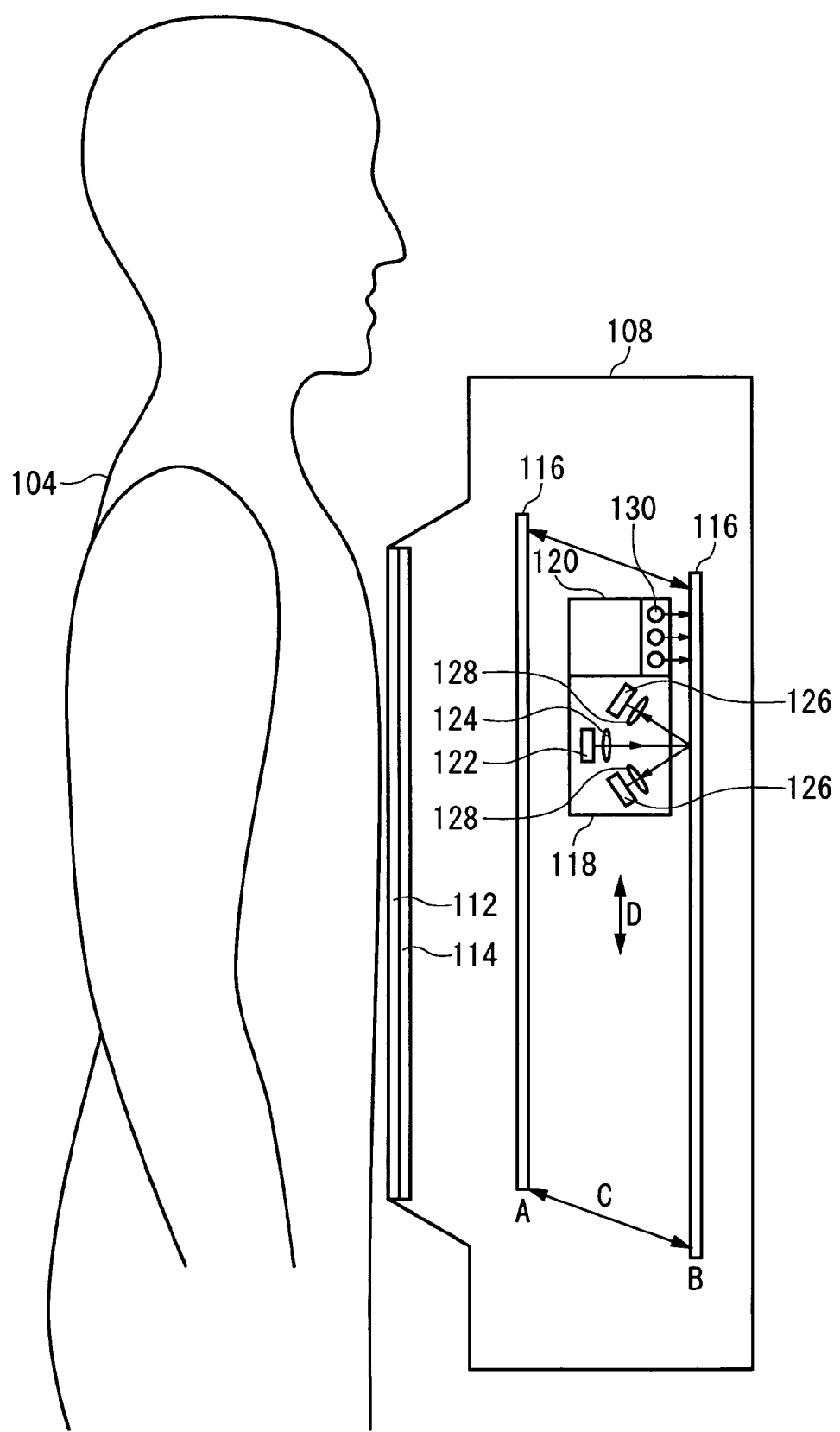
FIG. 2 is a side view exemplary showing a configuration of a radiographic image receiving section.

FIG. 2 is a side view exemplary showing a configuration of the radiographic image receiving section 108 according to the present embodiment. The radiographic image receiving section 108 includes: a timer 112 for controlling dose of radiation to the radiographic image receiving section 108; a grid 114 for eliminating scattered radiation; a photostimulable phosphor plate 116 for absorbing the radiation which transmitted through the object 104, the timer 112, and the grid 114, and for storing radiographic image information; a reading unit 118 for reading the radiographic image information from the photostimulable phosphor plate 116; and an erasing unit 120 for erasing the radiographic image information stored on the photostimulable phosphor plate 116.

The reading unit 118 includes: an excitation light source 122 for generating excitation light; a focusing optical system 124 for focusing the excitation light onto the photostimulable phosphor plate 116; a plurality of line sensors 126 for detecting photostimulated luminescence emitted by exiting the photostimulable phosphor plate 116 by the excitation light; and a plurality of condensing optical systems 128 for condensing the photostimulated luminescence light on each of the plurality of line sensors 126. Moreover, the erasing unit 120 includes a plurality of erasing light sources 130 for generating erasing light.

The photostimulable phosphor plate 116 is placed so that it is movable in the direction of arrow C between an imaging position A and a reading position B by a drive mechanism (not shown). When the photostimulable phosphor plate 116 is positioned at the imaging position A, the photostimulable phosphor plate 116 absorbs the radiation which transmitted through the object 104, the timer 112, and the grid 114, and stores the radiographic image.

The reading unit 118 and the erasing unit 120 are placed so that they are movable in the direction of arrow D by a drive mechanism (not shown). When the photostimulable phosphor plate 116 is positioned at the reading position B, the reading unit 118 emits excitation light to the photostimulable phosphor plate 116, moving along with the photostimulable phosphor plate 116, and reads the radiographic image information by detecting the photostimulated luminescence emitted from the photostimulable phosphor plate 116. The radiographic image read from the photostimulable phosphor plate 116 by the reading unit 118 is recorded as digital data. Moreover, the erasing unit 120 emits erasing light to the photostimulable phosphor plate 116, moving with the reading unit 118 along with the photostimulable phosphor plate 116, and erases the radiographic image information by freeing the remaining radiation energy on the photostimulable phosphor plate 116.

Figure 3:
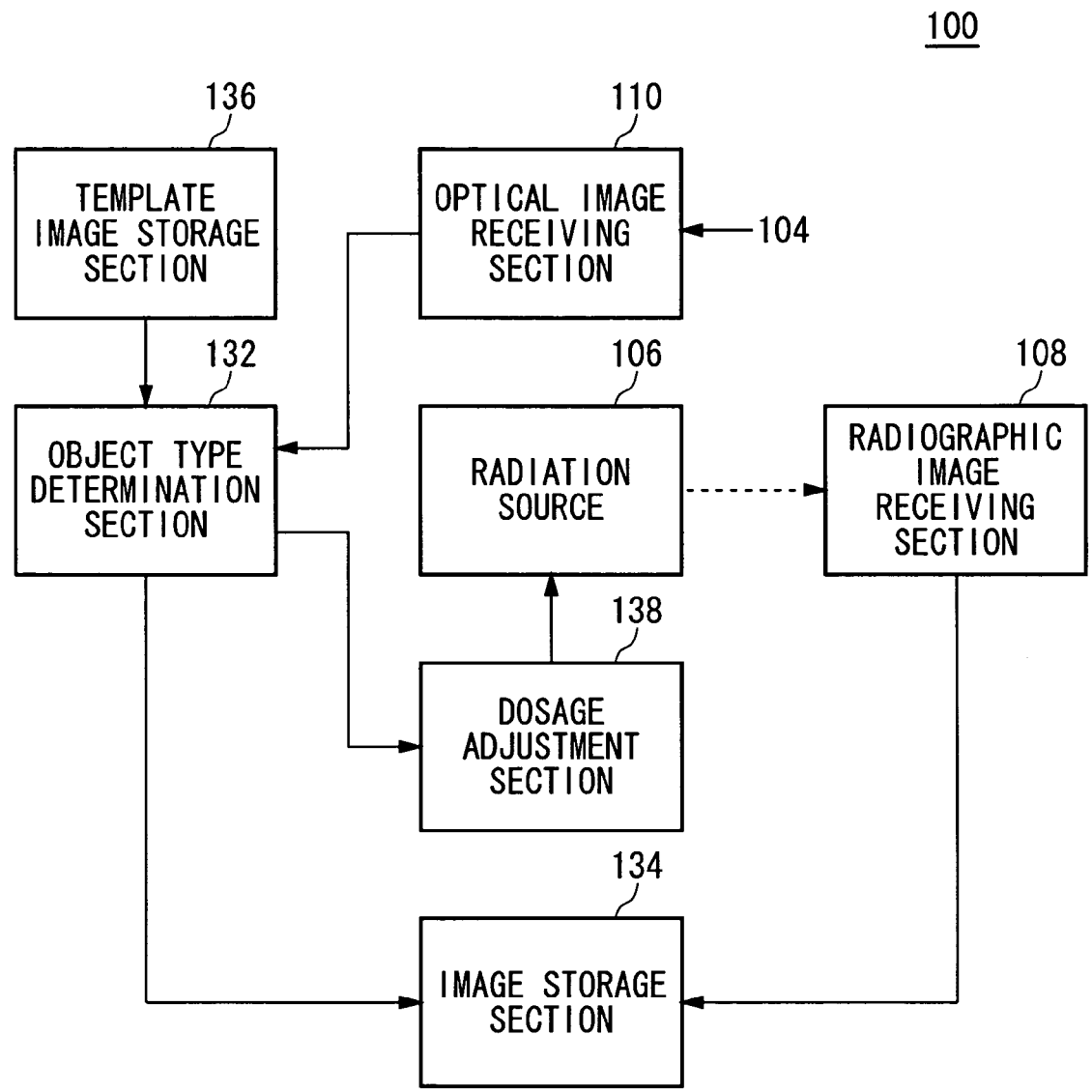
FIG. 3 is a block diagram exemplary showing a configuration of the radiography system.

FIG. 3 is a block diagram exemplary showing a configuration of the radiography system 100 according to the present embodiment. The radiography system 100 includes: the radiation source 106 for generating the radiation 102 and irradiating the radiation 102 to the object 104; the radiographic image receiving section 108 for receiving the radiographic image of the object 104 using the radiation 102; the optical image receiving section 110 for detecting the light emitted from the object 104 and receiving the optical image of the object 104; an object type determination section 132 for determining the type of the object 104; an image storage section 134 storing thereon the radiographic image received by the radiographic image receiving section 108 in association with the object type determined by the object type determination section 132; a template image storage section 136 storing thereon template images of object types; and a dosage adjustment section 138 for adjusting the dose of radiation irradiating from the radiation source 106 to the object 104. The object type indicates the imaging direction from which the object 104 is taken, the imaging area of the object 104, etc.

The object type determination section 132 determines the imaging direction indicating the direction from which the radiographic image of the object 104 received by the radiographic image receiving section 108 is taken based on the optical image received by the optical image receiving section 110. For example, if image of face or eyes of the patient are included in the optical image received by the optical image receiving section 110, the object type determination section 132 determines that the radiographic image is taken by irradiating the radiation 102 from front to back of the patient (AP). Moreover, if image of fingernail is included in the optical image received by the optical image receiving section 110, the object type determination section 132 determines that the radiographic image is taken by irradiating the radiation 102 from dorsum to palm of the patient's hand (PA). Then, the image storage section 134 stores the radiographic image received by the radiographic image receiving section 108 in association with the imaging direction determined by the object type determination section.

Moreover, the object type determination section 132 determines the imaging area indicating the area of the object 104 on the radiographic image received by the radiographic image receiving section 108 based on the optical image received by the optical image receiving section 110. For example, if image of eyes, of which the size is more than a predetermined size, is included in the optical image received by the optical image receiving section 110, the object type determination section 132 determines that the objects 104 are face and head. Moreover, if image of fingernail or toenail, of which the size is more than a predetermined size, is included in the optical image received by the optical image receiving section 110, the object type determination section 132 determines that the objects 104 are hand or leg. Then, the image storage section 134 stores the radiographic image received by the radiographic image receiving section 108 in association with the imaging area determined by the object type determination section 132.

In this way, the imaging direction and the imaging area is accurately determined by using the optical image received by the optical image receiving section 110. Moreover, since the accurately determined imaging direction and the imaging area are stored in association with the radiographic image, appropriate diagnosis is provided for the patient.

The dosage adjustment section 138 adjusts the dose of radiation irradiating from the radiation source 106 to the object 104 based on the object type determined by the object type determination section 132. Specifically, the dosage adjustment section 138 adjusts the dose of radiation irradiating from the radiation source 106 to the object 104 based on the imaging direction or the imaging area. For example, when taking the radiographic image of a hand, the dose of the radiation is adjusted to be greater than the dose of the radiation when taking the radiographic image of a chest. Moreover, when the radiographic image of the patient is taken in lateral position, the dose of the radiation is adjusted to be grater than the dose of the radiation when acquiring the radiographic image of the patient taken in PA or AP position. Then, after the dosage adjustment section 138 adjusts the dose of the radiation 102, the radiographic image receiving section 108 receives the radiographic image of the object 104.

In this way, since the dosage adjustment section 138 adjusts irradiation time, tube voltage, tube electric current, etc. for the radiation 102 in accordance with the depth of the object 104, the dose of the radiation 102 irradiating to the object 104 is appropriately adjustable. Therefore, the high resolution radiographic image is acquirable while preventing overdose of the radiation 102 to the object 104.

Moreover, as shown in FIG. 1, it is preferable that the area of the optical image received by the optical image receiving section 110 surrounds the area of the radiographic image to be received by the radiographic image receiving section 108. For example, when the radiographic image receiving section 108 receives the radiographic image of chest, it is preferable that the optical image receiving section 110 receives the optical image of upper half of the body. Accordingly, though it is difficult to determine the imaging direction using the optical image of the chest, the imaging direction can be determined using the optical image of the upper half of the body.

Moreover, as shown in FIG. 1, it is preferable that the optical image receiving section 110 receives the optical image including an image of the object 104 and also an image of an area surrounding the object 104. For example, when the radiographic image receiving section 108 receives the radiographic image of arm, it is preferable that the optical image receiving section 110 receives the optical image including the arm and hand. Accordingly, though it is difficult to determine the imaging area using the optical image of the arm, the imaging area can be determined using the optical image of the hand or the fingernail.

In these two cases, the area of the optical image received by the optical image receiving section 110 encompasses the area of the radiographic image to be received by the radiographic image receiving section 108. Therefore, the optical image receiving section 110 receives the optical image which records the area corresponding to the area of the radiographic image received by the radiographic image receiving section 108, and the other area, i.e., the outer area of the radiographic image.

For example, the relative position among the radiation source 106, the optical image receiving section 110 and the radiographic image receiving section 108 are fixed. In this condition, when the focal length of the optical image receiving section is set to a predetermined value, relative position between the area of the optical image received by the optical image receiving section 110 and the area of the radiographic image received by the radiographic image receiving section 108 is fixed. Therefore, these two areas, i.e., the area corresponding to the area of the radiographic image received by the radiographic image receiving section 108, and the other area, are distinguishably recorded on the optical image received by the optical image receiving section 110.

Alternatively, four marks are placed on four corners of the radiographic image receiving section 108, so that these two areas are distinguishably recorded on the optical image received by the optical image receiving section 110 by receiving the image of the four corners with the image of the object 104.

FIG. 5 is a table showing data structure of data stored on the image storage section 134. The data storage section 134 includes: an ID number storage region 500 storing thereon ID numbers of the radiographic images; an imaging area storage region 501 storing thereon information on the imaging area of the radiographic images; an imaging direction storage region 502 storing thereon information on the imaging direction of the radio graphic images; a radiographic image storage region 503 storing thereon image data of the radio graphic images; and an incidental data storage region 504 storing thereon incidental information about the radiographic images, such as patient's names.

Referring to FIG. 1 and FIG. 5, the process of taking a radiographic image of chest of the object 104 in PA direction will be explained hereinafter to exemplify the present embodiment.

The object 104, i.e., a patient, stands towards the radiographic image receiving section 108.

The optical image receiving section 110 receives the optical image of upper half of the body of the object 104 and the radiographic image receiving section 108 receives the radiographic image of chest of the object 104 simultaneously from the back of the object 104 (PA).

As described above, since the area corresponding to the area of the radiographic image received by the radiographic image receiving section 108 (to be referred to as "area A" hereinafter), and the other area (to be referred to as "area B" hereinafter), are distinguishably recorded on the optical image received by the optical image receiving section 110, the object type determination section 132 determines from the optical image received from the optical image receiving section 110 that the imaging area is chest using the relative position between the area A and the area B, and pattern recognition technique, for example.

However, since there are few distinguishing parts on the trunk of the human body compared with the head of the body, it is difficult for the object type determination section 132 to determine the imaging direction (to determine whether the direction is PA or AP) using the optical image of the chest and/or back. Therefore, the optical image of the head will be used for determining the imaging direction.

For example, when the image of the eyes is identified from the optical image received by the optical image receiving section 110, the object type determination section 132 determines that the imaging direction is AP direction. When the image of an ear canal is identified from the optical image received by the optical image receiving section 110, the object type determination section 132 determines that the imaging direction is lateral direction. When neither the image of the eyes nor the ear canal is identified from the optical image, the object type determination section 132 determines that the imaging direction is PA direction.

In this example, the object 104, i.e., the patient, stands toward the radiographic image receiving section 108, i.e., stands with his/her back to the optical image receiving section 110 and the radiation source 106. Therefore, neither the image of the eyes nor the ear canal will be identified from the optical image received by the optical image receiving section 110. Accordingly, the object type determination section 132 determines that the imaging direction is PA direction judged from the optical image received from the optical image receiving section 110.

Then the object type determination section 132 outputs the information indicating the imaging area and the imaging direction of the object 104 determined by the object type determination section 132 to the image storage section 134, and the radiographic image receiving section 108 outputs image data of the radiographic image of the object 104 to the image storage section 134.

The image storage section 134 stores the information indicating the imaging area of the object 104 received from the object type determination section 132 on the imaging area storage region 501, the information indicating the imaging direction of the object 104 received from the object type determination section 132 on the imaging direction storage region 502, and the image data of the radiographic image of the object 104 received from the radiographic image receiving section 108 on the radiographic image storage region 503, all of which are associated with an ID number which has been allocated in the ID number storage region 500 in advance.

In addition, the incidental information, such as name of the object 104, i.e., the patient's name, maybe manually stored on the incidental data storage region 504 in association with the ID number by a doctor or a radiological technician using a computer system. Therefore, incorrect recording of the object type is prevented, and appropriate diagnosis is provided to the patient. The methods is well known to those skilled in the art and would require only standard techniques to apply it to the system of the present invention.

FIGS. 4A to 4F are examples of template images stored on the template image storage section 136. For example, as shown in FIGS. 4A to 4F, the template image storage section 136 stores template images, such as images of left hand, right hand, head (AP), head (lateral), chest, and arm, respectively. In this case, the object type determination section 132 determines the object type by comparing the optical image received by the optical image receiving section 110 with each of the template images stored on the template image storage section 136.

In this example, the template images depicted in FIG. 4A to FIG. 4D are used for determining the imaging direction (PA, AP, lateral, etc.) of the object 104.

When a part of the optical image received by the optical image receiving section 110 is similar to one of the template images depicted in FIGS. 4A to 4D stored on the template image storage section 136, the object type determination section 132 selects the template image and determines the imaging direction based on the selected template image.

Moreover, each of the template images depicted in FIGS. 4A to 4D includes identification information (not shown) indicating the imaging direction. For example, the template image shown in FIG. 4C includes identification information indicating that the imaging direction is AP direction.

Figure 4A:
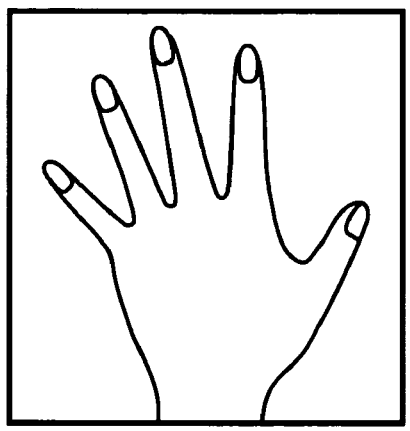
FIGS. 4A to 4F are examples of template images stored on a template image storage section.
Figure 4B:
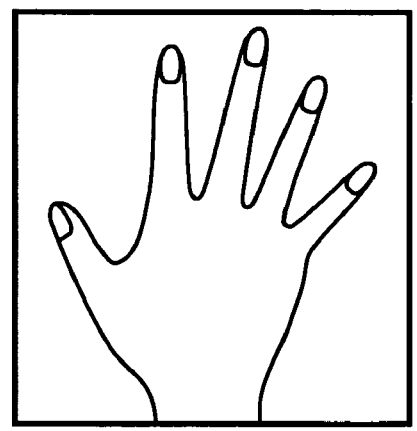
Figure 4C:
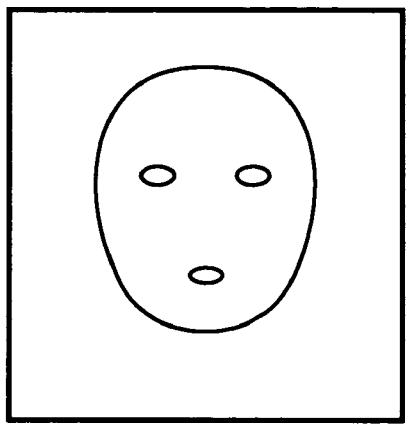
Figure 4D:
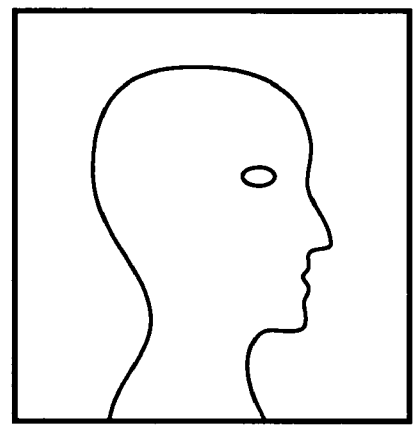

For example, when a part of the optical image received by the optical image receiving section 110 is similar to the template image shown in FIG. 4C, the object type determination section 132 selects the template image shown in FIG. 4C and determines that the imaging direction of the radiographic image is AP direction based on the identification information included in the template image shown in FIG. 4C.

After the object type determination section 132 determines the imaging direction based on the selected template image, the object type determination section 132 outputs the identification information included in the selected template image to the imaging direction storage region 502 of the image storage section 134 as the information on the imaging area.

Figure 4E:
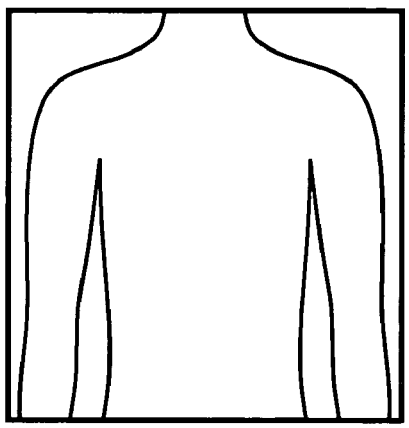
Figure 4F:
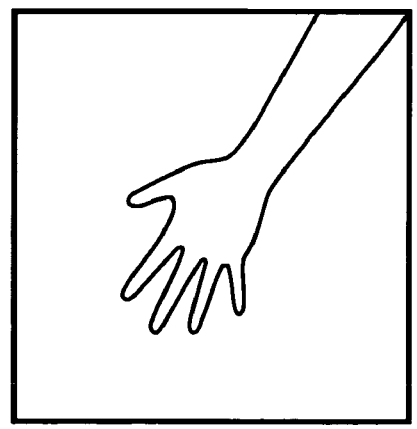

The template images depicted in FIGS. 4E and 4F are used for determining the imaging area of the object 104.

When at least a part of the optical image, which corresponds to the area of the radiographic image received by the radiographic image receiving section 108, received by the optical image receiving section 110 is similar to one of the template images depicted in FIGS. 4E and 4F stored on the template image storage section 136, the object type determination section 132 selects the template image and determines the imaging area based on the selected template image.

Moreover, each of the template images depicted in FIG. 4E and FIG. 4F includes identification information (not shown) indicating the imaging area of the radiographic image. For example, the template image shown in FIG. 4E includes identification indicating that the imaging area is chest.

For example, when the part of the optical image, which corresponds to the area of the radiographic image, received by the optical image receiving section 110 is similar to the template image shown in FIG. 4E, the object type determination section 132 selects the template image shown in FIG. 4E and determines that the imaging area of the radiographic image is chest based on the identification information included in the template image shown in FIG. 4E.

After the object type determination section 132 determines the imaging area based on the selected template image, the object type determination section 132 outputs the identification information included in the selected template image to the imaging area storage region 501 of the image storage section 134 as the information on the imaging area.

In this way, the object type of the object 104 is determined more accurately by using the template images.

In another example, when the radiographic image of the object including plenty of distinguishing parts, such as head, is to be taken, i.e., when the radiography system according to the present invention is to be applied to the radiography apparatus dedicated to take the radiographic image of skull or the like, the object type determination section 132 can determine the imaging direction from the optical image of the object itself using pattern matching technique, comparison of the template image and the optical image of the object, or the like. In such a case, the area of the optical image received by the optical image receiving section 110 does not have to be larger than the area of the radiographic image to be received by the radiographic image receiving section 108. Accordingly, the area of the optical image received by the optical image receiving section 110 is substantially the same as that of the radiographic image to be received by the radiographic image receiving section 108.

According to the examples described above, the information on the imaging area and the imaging direction determined by the object type determination section 132 is stored on the image storage section 134 in association with the radiographic image received by the radiographic image receiving section 108. However, in another example, the optical image received by the optical image receiving section 110 is stored on the image storage section 134 in association with the radiographic image, so that a doctor or a radiological technician may see the optical image and the associated radiographic image to determine the imaging direction and the imaging area by him/herself. In this case, the patient retains a name plate, a number tag or the like, which is to be taken by the optical image receiving section 110 when receiving the optical image and the radiographic image of the patient, so that the doctor or the radiological technician may manually stores the incidental information on the patient on the incidental data storage region 504 in association with the ID number according to the information on the name plate, number tag or the like taken on the optical image. Also in this case, the object type of the object 104 is determined accurately.

As described above, according to the present invention, there are provided the radiography system and the machine readable medium storing program for accurately determining the type of the object taken by the radiography.

Although the present invention has been described by way of an exemplary embodiment, it should be understood that those skilled in the art might make many changes and substitutions without departing from the spirit and the scope of the present invention. It is obvious from the definition of the appended claims that embodiments with such modifications also belong to the scope of the present invention.

What is claimed is:

1. A radiography system for acquiring a radiographic image a penetrating radiation source of an object using radiation, comprising:

a radiographic image receiving section for receiving the radiographic image of the object using the radiation;

an optical image receiving section for detecting light from the object, and for receiving the optical image of the object;

an object type determination section for determining an object type of the radiographic image received by said radiographic image receiving section based on the optical image received by said optical image receiving section; and an image storage section storing thereon the radiographic image received by said radiographic image receiving section in association with the object type determined by said object type determination section, and for storing the radiographic image and the object type, being associated with each other.

2. The radiography system as claimed in claim 1, wherein said object type determination section determines a direction from which the radiographic image of the object, which is received by said radiographic image receiving section, is taken based on the optical image received by said optical image receiving section, and said image storage section stores the radiographic image received by said radiographic image receiving section in association with the imaging direction determined by said object type determination section.

3. The radiography system as claimed in claim 1, wherein said object type determination section determines an area of the object on the radiographic image received by said radiographic image receiving section based on the optical image received by said optical image receiving section, and said image storage section stores the radiographic image received by said radiographic image receiving section in association with the imaging area determined by said object type determination section.

4. The radiography system as claimed in claim 1, further comprising a template image storage section storing thereon a plurality of template images, each of which is associated with the object type, wherein said object type determination section determines the object type by comparing the optical image received by said optical image receiving section with each of the plurality of template images stored on said template image storage section.

5. The radiography system as claimed in claim 1, wherein an area of the optical image received by said optical image receiving section surrounds an area of the radiographic image to be received by said radiographic image receiving section.

6. The radiography system as claimed in claim 1, wherein said optical image receiving section receives the optical image including an image of the object and an image of an area surrounding the object.

7. The radiography system as claimed in claim 1, wherein an area of the optical image received by said optical image receiving section is substantially the same as an area of the radiographic image to be received by said radiographic image receiving section.

8. The radiography system as claimed in claim 1, further comprising a dosage adjustment section for adjusting dose of the radiation irradiating to the object in accordance with the object type determined by said object type determination section, wherein
    said radiographic image receiving section receives the radiographic image of the object after said dosage adjustment section adjusts the dose of the radiation.

9. A machine readable medium storing thereon a program for causing a radiography system to acquire a radiographic image of an object using penetrating radiation, the program comprising modules configured to execute steps of:
    receiving the radiographic image of the object using the radiation;
    receiving the optical image of the object by detecting light emitted from the object;
    determining an object type of the radiographic image received in said radiographic image receiving step based on the optical image received by in said optical image receiving step;
    associating the radiographic image received in said radiographic image receiving step with the object type determined in said object type determination section; and
    storing the radiographic image and the object type, being associated with each other in said associating step.

10. The machine readable medium as claimed in claim 9, further comprising a module configured to execute a step of adjusting dose of the radiation irradiating to the object in accordance with the object type determined in said object type determination step, wherein
    said radiographic image receiving step is conducted after said dosage adjustment step.

* * * * *